United States Patent
Coursey et al.

(10) Patent No.: US 9,109,961 B2
(45) Date of Patent: Aug. 18, 2015

(54) COMPOUND CALIBRATOR FOR THERMAL SENSORS

(75) Inventors: Johnathan S. Coursey, Germantown, MD (US); Kenton C. Hasson, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 631 days.

(21) Appl. No.: 13/223,270

(22) Filed: Aug. 31, 2011

(65) Prior Publication Data
US 2012/0051390 A1 Mar. 1, 2012

Related U.S. Application Data

(60) Provisional application No. 61/378,591, filed on Aug. 31, 2010.

(51) Int. Cl.
*G01K 15/00* (2006.01)
*G01K 11/06* (2006.01)

(52) U.S. Cl.
CPC .............. *G01K 15/00* (2013.01); *G01K 15/005* (2013.01)

(58) Field of Classification Search
CPC ..... G01K 15/00; G01K 15/002; G01K 11/06; G01K 13/00; G01K 15/005; G01K 5/00; C12Q 2565/629; C12Q 1/6844; C12Q 1/68; C12Q 2527/101; C12Q 2527/107; C12Q 3/00; C12Q 2563/185
USPC .............. 374/1, 2, 3, 161, 137, 185, 141, 10, 374/100, 160; 435/286.1, 283.1, 6.12, 3, 435/287.2
See application file for complete search history.

(56) References Cited

U.S. PATENT DOCUMENTS

| | | | | |
|---|---|---|---|---|
| 4,627,740 A | * | 12/1986 | Jerde et al. | 374/1 |
| 5,265,957 A | * | 11/1993 | Moslehi et al. | 374/1 |
| 5,475,610 A | | 12/1995 | Atwood et al. | |
| 6,561,694 B1 | * | 5/2003 | Lerch et al. | 374/126 |
| 6,676,287 B1 | * | 1/2004 | Mathis et al. | 374/1 |
| 6,769,803 B1 | * | 8/2004 | Feichtinger et al. | 374/1 |
| 6,908,224 B2 | * | 6/2005 | Schneider et al. | 374/1 |
| 7,504,241 B2 | | 3/2009 | Atwood et al. | |

(Continued)

FOREIGN PATENT DOCUMENTS

| | | | |
|---|---|---|---|
| GB | 2215839 A | * | 9/1989 |
| JP | H06-233670 A | | 8/1994 |

OTHER PUBLICATIONS

Seipp et al., 2007, "Unlabeled Oligonucleotides as Internal Temperature Controls for Genotyping by Amplicon Melting," J. Molecular Diagnostics, vol. 9, No. 3, pp. 284-289.

(Continued)

*Primary Examiner* — Gail Kaplan Verbitsky
(74) *Attorney, Agent, or Firm* — Rothwell, Figg, Ernst & Manbeck, P.C.

(57) ABSTRACT

The present invention, in one aspect, provides a method for calibrating thermal control elements in situ using a single compound calibrator. In some embodiments, the present invention uses a compound calibrator to calibrate thermal control elements on a microfluidic device. In non-limiting embodiment, the compound calibrator can be a droplet, plug, slug, segment or continuous flow of any appropriate solution that, when heated, yields a thermal response profile with a plurality of features (e.g., maxima, minima, inflection points, linear regions, etc.).

18 Claims, 11 Drawing Sheets

(56) References Cited

U.S. PATENT DOCUMENTS

| | | | |
|---|---|---|---|
| 7,534,028 B2 * | 5/2009 | Jussel et al. | 374/1 |
| 7,572,051 B2 * | 8/2009 | Limb et al. | 374/1 |
| 7,677,794 B2 * | 3/2010 | Kim et al. | 374/1 |
| 8,556,501 B2 * | 10/2013 | Topham et al. | 374/2 |
| 8,794,831 B2 * | 8/2014 | Coursey et al. | 374/185 |
| 2003/0224464 A1 | 12/2003 | Thompson | |
| 2004/0247013 A1 * | 12/2004 | Clark et al. | 374/1 |
| 2007/0026421 A1 | 2/2007 | Sundberg et al. | |
| 2007/0206653 A1 * | 9/2007 | Nakano et al. | 374/1 |
| 2007/0231799 A1 | 10/2007 | Knight et al. | |
| 2008/0013591 A1 * | 1/2008 | Kim et al. | 374/1 |
| 2008/0130971 A1 | 6/2008 | Hasson et al. | |
| 2009/0037117 A1 | 2/2009 | Cheng | |
| 2009/0061489 A1 | 3/2009 | Hanagata et al. | |
| 2009/0080490 A1 * | 3/2009 | Mowry et al. | 374/1 |
| 2009/0143233 A1 | 6/2009 | Knight et al. | |
| 2009/0204353 A1 | 8/2009 | Cheng et al. | |
| 2009/0318306 A1 | 12/2009 | Hasson et al. | |
| 2010/0103975 A1 * | 4/2010 | Harslund et al. | 374/1 |
| 2012/0178077 A1 * | 7/2012 | DeCastro et al. | 435/3 |

OTHER PUBLICATIONS

Dodge et al., "A Microfluidic Platform Using Molecular Beacon-Based Temperature Calibration for Thermal Dehybridization of Surface-Bound DNA," Analytical Chemistry, American Chemical Society, vol. 76, No. 6, pp. 1778-1787, XP001196659 (Mar. 15, 2004).

* cited by examiner

COMPOUND CALIBRATOR FOR THERMAL SENSORS

CROSS-REFERENCE TO RELATED APPLICATION

The present application claims the benefit of priority to U.S. provisional patent application Ser. No. 61/378,591, filed on Aug. 31, 2010, the entire disclosure of which is incorporated herein by reference.

BACKGROUND

1. Field of the Invention

The present invention relates to systems and methods for calibrating thermal sensors. More particularly, aspects of the present invention relate to systems and methods for using a compound calibrator to calculate a relationship between temperature and an electrical characteristic of the thermal sensor for use in connection with calibrating thermal sensors.

2. Description of the Background

Devices for performing chemical, biological, or other reactions (e.g., a microfluidic device for performing polymerase chain reaction (PCR) amplification of DNA molecules, or a microfluidic molecular diagnostic platform that performs PCR on a patient sample and then uses the PCR product for genotyping by performing a high resolution melt analysis) often feature one or more thermal control elements that are used to subject reactants to a desired thermal profile. A description of PCR amplification, and an example of one possible microfluidic device including thermal control elements for PCR amplification and thermal melt analysis, are provided in U.S. patent application Ser. No. 12/165,043, which is hereby incorporated herein by reference.

In many applications of such microfluidic devices (e.g., PCR and/or thermal melt analysis), the thermal control elements of those devices must be precisely calibrated. That is, the correspondence between the temperature of the thermal control element and an electrical characteristic of the thermal control element must be precisely determined. For example, in the case of a resistance temperature detector, the correspondence between temperature and resistance must be precisely determined. Additional types of thermal control elements can include platinum resistive heaters, thermistors, diode temperature sensors, thermocouples, or any other suitable temperature measuring devices. Additional electrical characteristics of thermal control elements that correspond to temperature can include capacitance or inductance of an element, frequency, pulse width, or amplitude of a signal, or other sensor characteristics known in the art. Methods of calibrating thermal control elements often include generating a lookup table or a series of coefficients that define a calibration equation, i.e., a lookup table or an equation relating the temperature of the thermal control element with the electrical characteristic.

Calibration can be performed by sending the device to a third party laboratory for taking accurate measurements and generating the lookup table or series of coefficients; however, this procedure is generally expensive and time consuming. Furthermore, for many devices (e.g., many common microfluidic devices) there may be many thermal control elements (e.g. dozens or even hundreds of heaters and sensors), each of which requires its own precise calibration, making third-party calibration impractical.

Accordingly, what is desired is robust calibration of thermal sensors that can be accurate, reduce downtime and maintain high throughput.

SUMMARY OF THE INVENTION

In one aspect, the present invention includes a method for calibrating a thermal control element. The method may comprise the steps of (a) providing a compound calibrator in thermal contact with the thermal control element, (b) utilizing the thermal control element to perform a thermal variation to generate a thermal response profile for the compound calibrator, (c) identifying a first feature of the thermal response profile and generating a first relation between a known temperature of the first feature and a first measurement value of the thermal control element, (d) identifying a second feature of the thermal response profile and generating a second relation between a known temperature of the second feature and a second measurement value of the thermal control element, and (e) calculating one or more calibration coefficients for the thermal control element based on the first and second relations.

In further embodiments, the thermal response profile may be a thermal melt curve. In a yet further embodiment, the first feature may correspond to a first melting temperature of the compound calibrator, and the second feature may correspond to a second melting temperature of the compound calibrator. In other embodiments, the measurement value may be the resistance of the thermal control element.

In other embodiments, the compound calibrator may be a mixture of two or more amplicons of a nucleic acid. The amplicons may be Ultra-Conserved Elements of the human genome, for example. In a further embodiment, the amplicons may be synthetically generated. In still another embodiment, the calibration coefficients may be the coefficients of a linear calibration equation. In still another embodiment, the first feature may be at a melting temperature of a first of the two or more amplicons in the compound calibrator, and the second feature may be at a melting temperature of a second of the two or more amplicons in the compound calibrator.

In a further embodiment, the method further comprises the steps of identifying a third feature of the thermal response profile, as well as generating a third relation between a known temperature of the third feature and a third measurement value of the thermal control element. In this embodiment, the step of calculating one or more calibration coefficients includes calculating one or more calibration coefficients for said thermal control element based on said first, second, and third relations. In an embodiment of this method, the calibration coefficients may be the coefficients of a quadratic calibration equation. In another embodiment of this method, the first feature is at a melting temperature of a first of three or more amplicons in the compound calibrator, the second feature is at a melting temperature of a second of the three or more amplicons in the compound calibrator, and the third feature is at a melting temperature of a third of the three or more amplicons in the compound calibrator. In another embodiment, one of the first, second, and third features may be at a melting temperature of a first amplicon in the compound calibrator, and the other two of the first, second, and third features are at melting temperatures of a second amplicon in the compound calibrator.

In another embodiment, the method may further include the additional steps of identifying a third relation between a known ambient temperature and a measurement value of the thermal control element. In this embodiment, the step of calculating one or more calibration coefficients may further be based on at least the first, second, and third relations.

Another embodiment of the invention includes a method for calibrating a plurality of thermal control elements in a thermal device. This method may include the steps of (a) providing a compound calibrator in a first thermal zone, wherein the first thermal zone is in thermal contact with a first of said plurality of thermal control elements, (b) utilizing the first thermal control element to perform a thermal variation, generating a first thermal response profile for the compound calibrator, (c) identifying a first feature of the first thermal response profile and generating a first relation between a known temperature of the first feature and a first measurement value of the first thermal control element, (d) identifying a second feature of the first thermal response profile and generating a second relation between a known temperature of the second feature and a second measurement value of the first thermal control element, (e) calculating one or more calibration coefficients for the first thermal control element based on at least the first and second relations; and f) repeating steps a-e using the compound calibrator in a second thermal zone, wherein the second thermal zone is in thermal contact with a second thermal control element.

In a further embodiment, the method may include repeating steps a-e for each additional thermal element in the thermal device. In a further aspect, the thermal device may be a microfluidic channel in thermal communication with a plurality of thermal control elements.

In a further embodiment, the first thermal zone may be thermally isolated from the second thermal zone. The first thermal zone and the second thermal zone may be calibrated in parallel. In another embodiment, the first thermal zone and the second thermal zone may be calibrated in series. In still another embodiment, the compound calibrator may be a mixture of two or more amplicons of a nucleic acid.

Another aspect of the present invention is a method for calibrating a plurality of thermal control elements in a thermal device. In this aspect, the method may include the steps of (a) providing a compound calibrator in a first thermal zone, wherein the first thermal zone is in thermal contact with a first of the plurality of thermal control elements, (b) utilizing the first thermal control element to perform a thermal variation, generating a first thermal response profile for the compound calibrator, (c) identifying a first feature of the first thermal response profile and generating a first relation between a known temperature of said first feature and a first measurement value of the first thermal control element, (d) identifying a second feature of the first thermal response profile and generating a second relation between a known temperature of the second feature and a second measurement value of the first thermal control element, (e) identifying a third relation between a known ambient temperature and measurement value of the first thermal control element, (f) calculating one or more calibration coefficients for the first thermal control element based on at least the first, second, and third relations, and (g) repeating steps a-f using the compound calibrator in a second thermal zone, wherein the second thermal zone is in thermal contact with a second thermal control element.

In another embodiment, a method for calibrating a thermal control element is provided which may include the steps of (a) providing a compound calibrator in thermal contact with the thermal control element, (b) utilizing the thermal control element to perform a thermal ramp, (c) generating a melt curve for the compound calibrator, (d) identifying a first feature of the melt curve and generating a first relation between a known temperature of the first feature and a first measurement value of the thermal control element, (e) identifying a second feature of the melt curve and generating a second relation between a known temperature of the second feature and a second measurement value of the thermal control element, and (f) calculating one or more calibration coefficients for the thermal control element based on at least the first and second relations.

In this embodiment, the method may further comprise identifying a third relation between a known ambient temperature and a third measurement value of the thermal control element, wherein the step of calculating one or more calibration coefficients is further based at least on the third relation.

In a further embodiment, a method for serially calibrating a plurality of thermal control elements in a microfluidic channel which may include the steps of (a) providing a compound calibrator in thermal contact with a first of the plurality of thermal control elements, (b) utilizing the first thermal control element to perform a thermal ramp, generating a first melt curve for the compound calibrator, (c) identifying a first feature of the first melt curve and generating a first relation between a known temperature of the first feature and a first measurement value of the first thermal control element, (d) identifying a second feature of the first melt curve and generating a second relation between a known temperature of the second feature and a second measurement value of the first thermal control element, (e) calculating one or more calibration coefficients for the first thermal control element based on at least the first and second relations, (f) providing the compound calibrator in thermal contact with a second of said plurality of thermal control elements, (f) utilizing the second thermal control element to perform a thermal ramp, generating a second melt curve for the compound calibrator, (g) identifying a third feature of the second melt curve and generating a third relation between a known temperature of the third feature and a third measurement value of the second thermal control element, (h) identifying a fourth feature of the second melt curve and generating a fourth relation between a known temperature of the second feature and a fourth measurement value of the second thermal control element, and (i) calculating one or more calibration coefficients for the second thermal control element based on at least the third and fourth relations.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF THE PREFERRED EMBODIMENTS

In one aspect, the present invention provides a method for calibrating thermal control elements in situ using a single compound calibrator. In some embodiments, the present invention uses a compound calibrator to calibrate thermal control elements on a microfluidic device. In a non-limiting embodiment, the compound calibrator can be a droplet, plug, slug, segment or continuous flow of any appropriate solution that, when heated, yields a thermal response profile with a plurality of features (e.g., maxima, minima, inflection points, linear regions, etc.).

The above and other aspects and features of the present invention, as well as the structure and application of various embodiments of the present invention, are described below with reference to the accompanying drawings.

Figure 1:
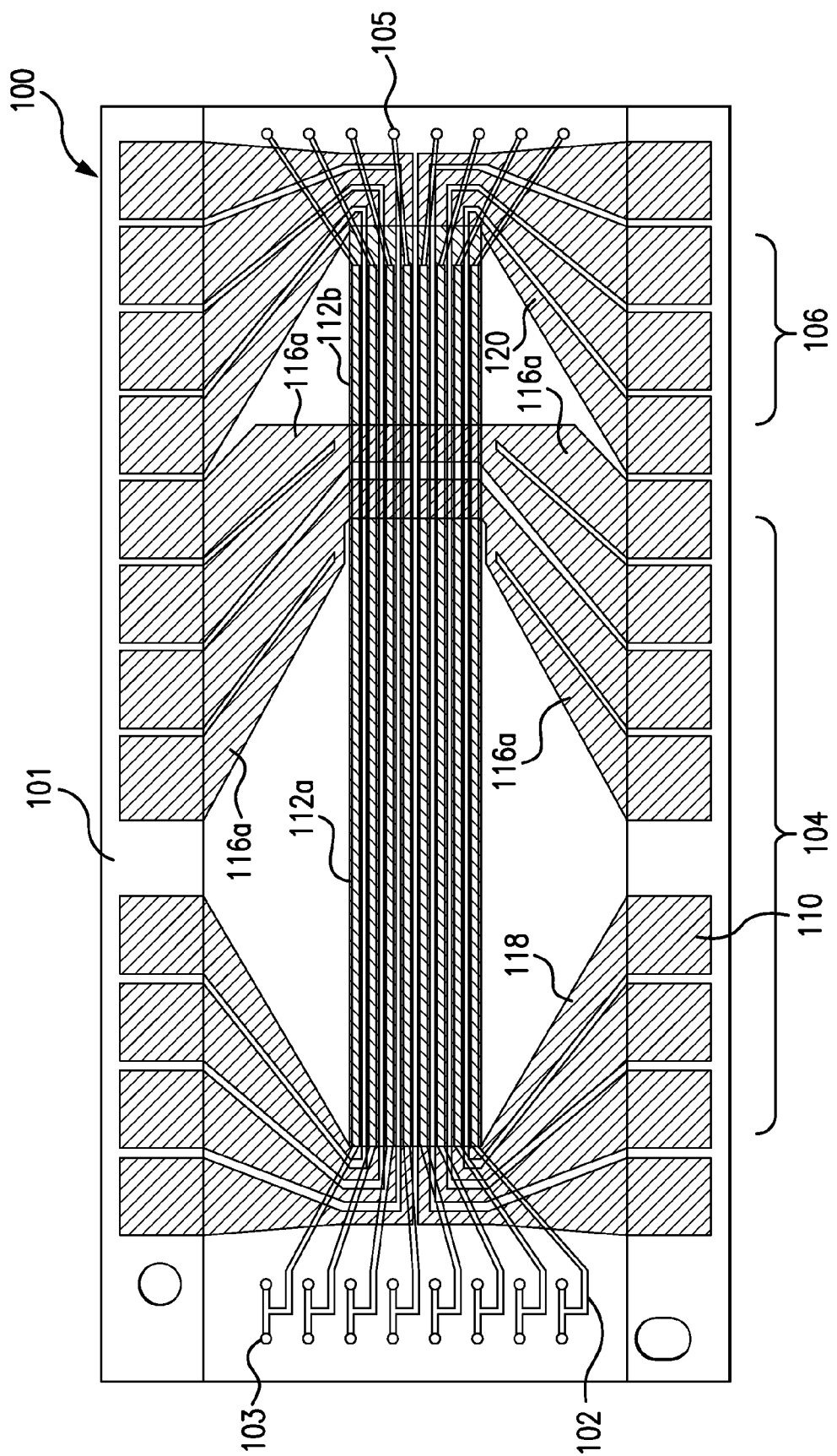
FIG. 1 illustrates a microfluidic device that can be used in conjunction with the methods of the present invention.

FIG. 1 illustrates a microfluidic device 100 that may be used in performing aspects of the present invention. It will be appreciated by those of skill in the art that other devices (including other microfluidic devices) also may be used in accordance with the present invention. Specifically, aspects of the present invention could be used in other molecular biological instruments, such as, for example, PCR instruments or other instruments requiring thermal calibration. In the illustrative embodiment of the microfluidic device, the microfluidic device 100 includes several microfluidic channels 102 extending across a substrate 101. Each channel 102 includes one or more inlet ports 103 (the illustrated embodiment shows two inlet ports 103 per channel 102) and one or more outlet ports 105 (the illustrated embodiment shows one outlet port 105 per channel 102). In exemplary embodiments, each channel may be subdivided into a first portion extending through a PCR thermal zone 104 (as described below) and a second portion extending through a thermal melt zone 106 (as described below).

In an embodiment, the microfluidic device 100 further includes thermal control elements in the form of thin film resistive heaters 112 associated with the microfluidic channels 102. In one non-limiting embodiment, the thin film resistive heaters 112 may be platinum resistive heaters whose resistances are measured in order to control their respective temperatures. In the embodiment illustrated in FIG. 1, each heater element 112 comprises two heater sections: a PCR heater section 112a in the PCR zone 104, and a thermal melt heater section 112b in the thermal melt zone 106.

The microfluidic device 100 may include a plurality of heater electrodes 110 connected to the various thin-film heaters 112a and 112b. In non-limiting embodiments, heater electrodes 110 may include PCR section leads 118, one or more PCR section common lead 116a, thermal melt section leads 120, and one or more thermal melt section common lead 116b. According to one embodiment of the present invention, a separate PCR section lead 118 is connected to each of the thin-film PCR heaters 112a, and a separate thermal melt section lead 120 is connected to each of the thin-film thermal melt heaters 112b.

Figure 2:
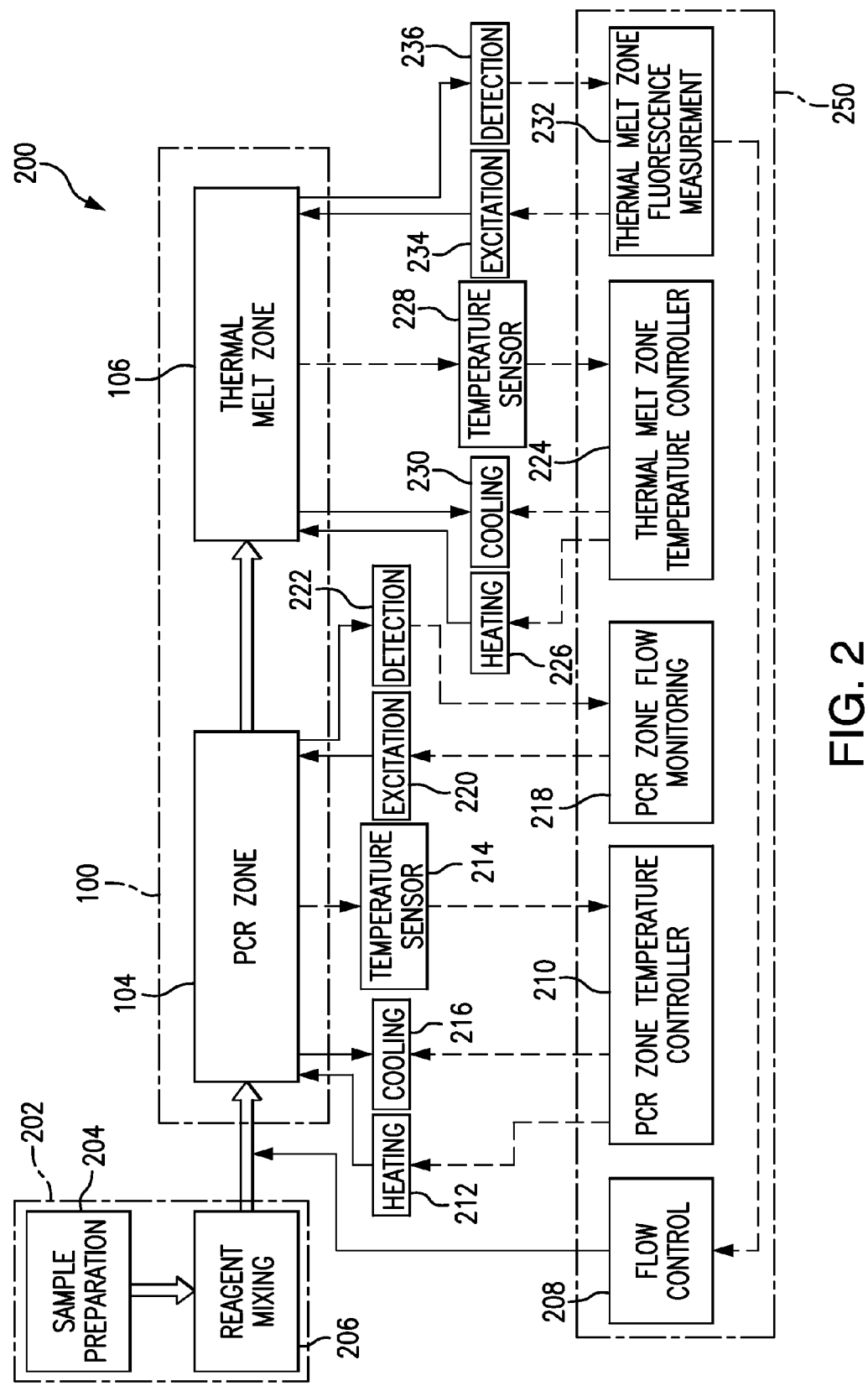
FIG. 2 is a functional block diagram of a system for using a microfluidic device that can be used in conjunction with the methods of the present invention.

FIG. 2 illustrates a functional block diagram of an exemplary system 200 for using a microfluidic device, such as microfluidic device 100. In the illustrated embodiment, the DNA sample is input in the microfluidic chip 100 from a preparation stage 202. The preparation stage 202 may comprise appropriate devices for preparing the sample 204 and for adding one or more reagents 206 to the sample. Once the sample is input into the microfluidic chip 100, e.g., at an input port 103, it flows through a channel 102 into the PCR zone 104 where PCR takes place. That is, as explained in more detail below, as the sample flows within a channel 102 through the PCR zone 104, it is exposed to the PCR temperature cycle a plurality of times to effect PCR amplification. Next, the sample flows into the thermal melt zone 106 where a high resolution thermal melt process occurs. Flow of sample into the microfluidic chip 100 can be controlled by a flow controller 208. In one embodiment, the flow controller may comprise one or more pressure monitoring devices (e.g., MEMS pressure sensors) and one or more pumping elements (e.g., peristaltic pumps). A control system 250 may comprise, for example, a flow controller 208, a PCR zone temperature controller 210, a PCR flow monitor 218, a thermal melt zone temperature controller 224, and a zone fluorescence measurement system 232.

The temperature in the PCR zone 104 can be controlled by the PCR zone temperature controller 210. The PCR zone temperature controller 210, which may be a programmed computer or other microprocessor, sends signals to the heater device 212 (e.g., a PCR heater 112a) based on the temperature determined by a temperature sensor 214 (such as, for example, an RTD or thin-film thermistor, or a thin-film thermocouple thermometer). In this way, the temperature of the PCR zone 104 can be maintained at the desired level. According to some embodiments of the present invention, the PCR zone 104 may also be cooled by a cooling device 216 (for example, to quickly bring the channel temperature from 92° C. down to 55° C.), which may also be controlled by the PCR zone temperature controller 210. In exemplary embodiments, the cooling device 216 could be a peltier device, heat sink or forced convection air cooled device, for example.

The flow of sample through the microfluidic channels 102 can be measured by a PCR zone flow monitoring system 218. In one embodiment, the flow monitoring system can be a fluorescent dye diffusion imaging and tracking system illustrated in U.S. patent application Ser. No. 11/505,358, incorporated herein by reference. According to one embodiment of the present invention, the channels in the PCR zone can be excited by an excitation device 220 and light fluoresced from the sample can be detected by a detection device 222. An example of one possible excitation device and detection device forming part of an imaging system is illustrated in U.S. patent application Ser. Nos. 11/606,006 and 11/505,358, incorporated herein by reference in their entireties.

The thermal melt zone temperature controller 224, e.g. a programmed computer or other microprocessor, can be used to control the temperature of the thermal melt zone 106. As with the PCR zone temperature controller 210, the thermal melt zone temperature controller 224 sends signals to the heating component 226 (e.g., a thermal melt heater 112b) based on the temperature measured by a temperature sensor 228 which can be, for example, an RTD or thin-film thermocouple. Additionally, the thermal melt zone 106 may be independently cooled by cooling device 230. In exemplary embodiments, the cooling device 230 could be a peltier device, heat sink or forced convection air cooled device, for example. The fluorescent signature of the sample can be measured by the thermal melt zone fluorescence measurement system 232. The fluorescence measurement system 232 excites the sample with an excitation device 234, and the fluorescence of the sample can be detected by a detection device 236. An example of one possible fluorescence measurement system is illustrated in U.S. patent application Ser. Nos. 11/606,006 and 11/505,358, incorporated herein by reference in their entireties.

In accordance with aspects of the present invention, the thin film heaters 112 may function as both heaters and temperature detectors. Thus, in one embodiment of the present invention, the functionality of heating element 212 and 226 and temperature sensors 214 and 228 can be accomplished by the thin film heaters 112.

In one embodiment, the system 200 sends power to the thin-film heaters 112a and/or 112b, thereby causing them to heat up, based on a control signal sent by the PCR zone temperature controller 210 or the thermal melt zone temperature controller 224. The control signal can be, for example, a pulse width modulation (PWM) control signal. An advantage of using a PWM signal to control the heaters 212 is that with a PWM control signal, the same voltage potential across the heaters may be used for all of the various temperatures required. In another embodiment, the control signal could utilize amplitude modulation or alternating current. In some embodiments, it may be advantageous to use a control signal that is amplitude modulated to control the heaters 212 because a continuous modest change in voltage, rather than large voltage steps, may avoid slew rate limits and improve settling time. Further discussion of amplitude modulation can be found in U.S. patent application Ser. No. 12/825,476, filed Jun. 29, 2010, which is incorporated herein by reference. In some embodiments, the desired temperature for the heaters is reached by changing the duty cycle of the control signal. For example, the duty cycle of the control signal for achieving 95° C. in a PCR heater might be about 50%, the duty cycle of the control signal for achieving 72° C. in a PCR heater might be about 25%, and the duty cycle of the control signal for achieving 55° C. in a PCR heater might be about 10%.

The microfluidic device 100 and the system 200 can be used in conjunction with aspects of the present invention. For example, one can use the microfluidic device 100 in connection with the system 200 described above to calibrate the heaters 112 on the microfluidic device 100 using a droplet, plug, slug, segment, or continuous flow of a compound calibrator, in accordance with aspects of the invention.

In some embodiments, calibration of a thermal control element can include determining the coefficients of a calibration equation, i.e., an equation that models the relationship between the temperature of the thermal control element and a measurement value. In an embodiment, that measurement value may be an electrical characteristic of the thermal control element. For example, a calibration equation for a resistive heater 112 may model the relationship between the temperature of the heater 112 and the resistance of the heater 112. In this embodiment, the calibration equation may model a linear relationship as shown in Equation 1:

$$T = k_0 + k_1 R \qquad \text{Equation 1}$$

In this case, T is temperature of the thermal control element, R is the resistance of the thermal control element, and $k_0$ and $k_1$ are constants (i.e., the coefficients) to be determined by calibration. Two calibration coefficients can be determined by, for example, measuring the resistance R at two known temperatures ($T_1$ and $T_2$). In some aspects of the present invention, these measurements can be obtained by heating the thermal control element (e.g., a heater 112) in thermal contact with a droplet, plug, slug, segment or continuous flow of a compound calibrator (e.g., while a compound calibrator is in a microfluidic channel 102 corresponding with the heater 112) and measuring the resistance of the thermal control element (e.g., measuring the resistance of the heater 112) at temperatures that coincide with two or more features of the thermal response profile of the compound calibrator.

In other embodiments, the calibration equation may model the relation between other electrical factors, such as the current, electric potential, applied power, resistivity, conductivity, or other related quantities. In some aspects, the measurement value may be an independently controlled aspect of the thermal control element that is related to the temperature of the thermal control element. In other aspects, the measurement value could be any factor related to the temperature of the thermal control element.

In some embodiments, the calibration equation may contain more coefficients to be determined. For example, in the case where the measurement value is resistance, some calibration equations can model a quadratic relationship as shown in Equation 2:

$$T = k_0 + k_1 R + k_2 R^2 \qquad \text{Equation 2}$$

In this case, a compound calibrator having three or more features in its thermal response profile is preferable to more accurately determine all of the coefficients. Further, one of ordinary skill will comprehend that this approach may be expanded for a compound calibrator having n or more features, using Equation 3:

$$T = k_0 + k_1 R + k_2 R^2 + \ldots k_{n-1} R^{n-1} \qquad \text{Equation 3}$$

Furthermore, in some embodiments, more accurate values for the coefficients may be obtained by utilizing a compound calibrator having more features than there are coefficients to be determined (i.e., determine more correspondences between temperature and resistance of the thermal control element than there are coefficients). The resulting over-determined system can be solved, for example, using the least squares method.

Figure 3:
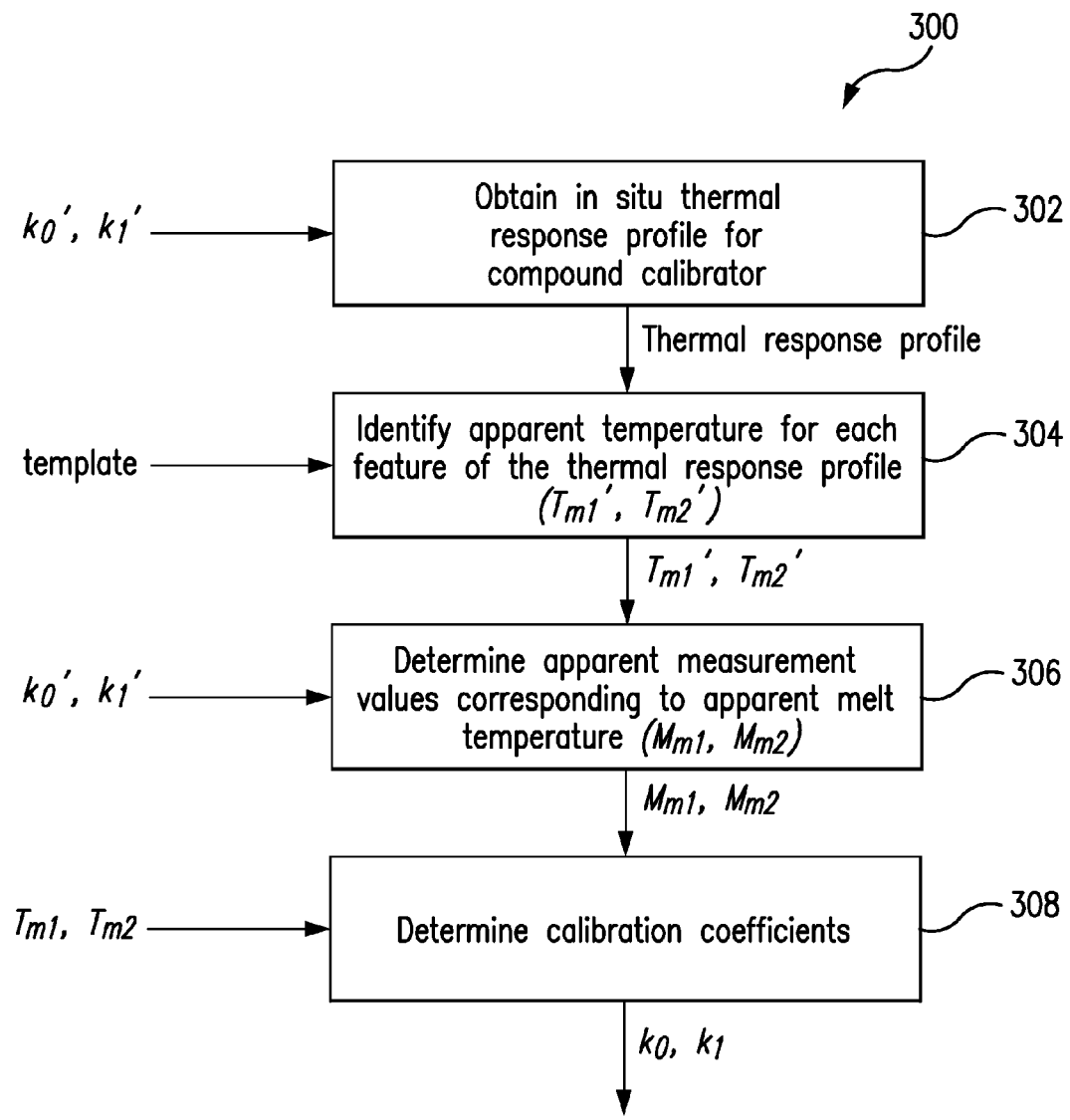
FIG. 3 illustrates a process for calibrating a thermal control element using a compound calibrator according to an embodiment of the present invention.

FIG. 3 illustrates a process 300 for calibrating a thermal control element using a compound calibrator, in accordance with an embodiment of the present invention. As will be explained in further detail below, the process 300 can be used to determine the coefficients of a calibration equation with a single droplet, plug, segment, or slug containing a compound calibrator. Alternatively, the process 300 can be used to determine the coefficients of a calibration equation with a continuous flow of calibrant.

The process 300 can begin at step 302 at which an in situ thermal response profile is obtained for the compound calibrator. As used herein, a "thermal response profile" refers to the analysis of a dependent variable related to a solution that is subject to a thermal variation, i.e., the relationship between a solution's temperature and the dependent variable. In some embodiments, the thermal response profile may be a "melt curve," i.e. the fluorescent melt analysis of a solution to determine the relationship between the amount of fluorescence and the solution's temperature. Other possible thermal response profiles may be based on the absorbance, transmittance, reflectance, or emissivity of the compound calibrator. In some embodiments, generating such a thermal response profile can include loading a microfluidic chip (e.g., the microfluidic chip 100) into a system for controlling reactions in the microfluidic chip (e.g., system 200), loading a droplet, plug, slug, segment, or continuous flow of the compound calibrator into the chip (e.g., into a microfluidic channel 102), and controlling a thermal control element that is in thermal communication with the compound calibrator (e.g., heater 112) to heat the compound calibrator while monitoring the temperature of the thermal control element and while monitoring the dependent variable (e.g., fluorescence in the case in which a melt curve is obtained) of the compound calibrator.

Figure 4:
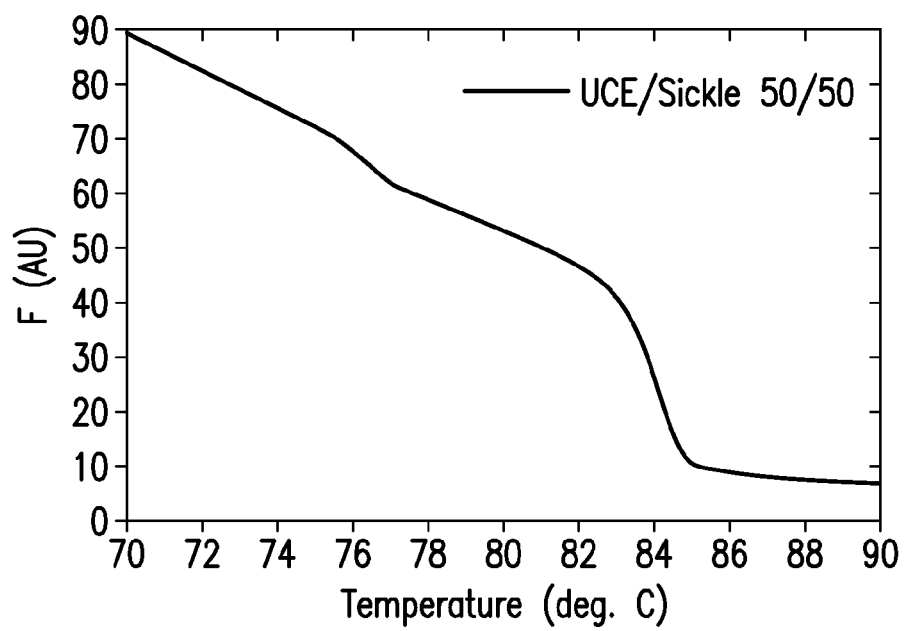
FIG. 4 is an exemplary melt curve for a compound calibrator that may be generated in connection with an embodiment of the present invention.
Figure 5:
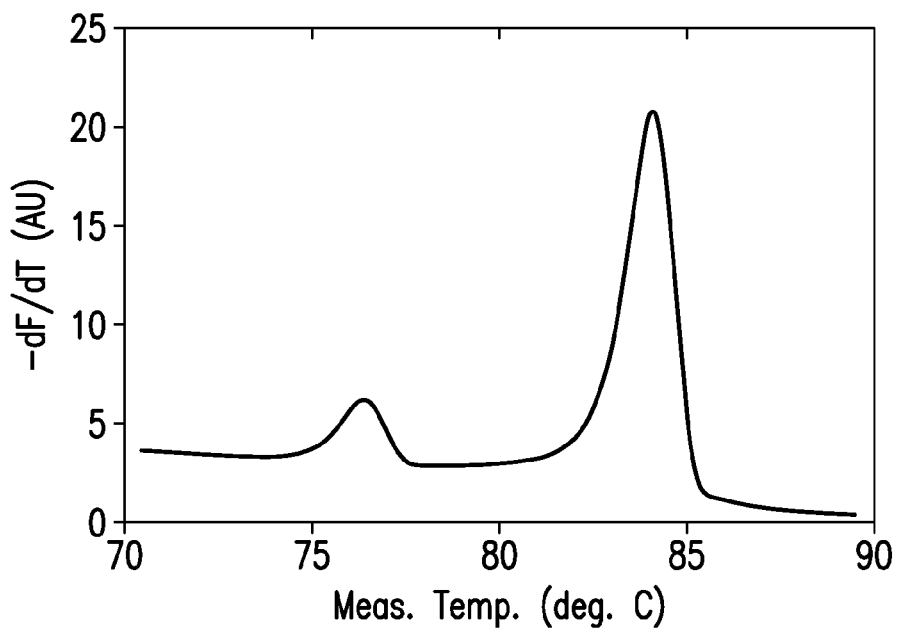
FIG. 5 is a derivative plot of a melt curve of a compound calibrator generated from the melt curve of FIG. 4.

In accordance with one embodiment, an initial estimate of the calibration coefficients (e.g., $k_0'$ and $k_1'$, which are respectively estimates of $k_0$ and $k_1$ of Equation 1) can be used to control the thermal control element for an initial thermal variation. The thermal variation may be any variation of the temperature of the thermal control element over a period of time. One example of such a thermal variation is a thermal ramp (e.g., heating the thermal control element at, for example, 0.5 degrees Celsius per second over a range of temperatures that includes temperatures corresponding to the features of the compound calibrator thermal response profile). During the thermal ramp, the dependent variable (e.g., fluorescence intensity) of the calibration plug (for example) and the measurement value of the thermal control element is monitored to generate a thermal response profile. FIG. 4 is an example of such a thermal response profile, which is a melt curve plotted as raw fluorescence as a function of temperature (i.e., F vs. T) using temperature values estimated by the initial estimated calibration coefficients (e.g., $k_0'$ and $k_1'$). In some embodiments, the thermal response profile may be displayed using data derived from raw measurements of the dependent variable and temperature data. For example, FIG. 5 illustrates a so called "derivative plot" which describes the derivative of fluorescence with respect to temperature as a function of temperature $$\left(\text{e.g.,} -\frac{\partial F}{\partial T} \text{ vs. } T\right).$$

In some embodiments, the derivative plot can be generated using a Savitsky-Golay filter. The melt curves illustrated in FIGS. 4 and 5 correspond to a compound calibrator containing a mixture of two amplicons (i.e., a compound calibrator having a two-feature melt curve). As described above, in other embodiments, a compound calibrator may have more than two amplicons or otherwise have a thermal response profile with more than two features.

Figure 6:
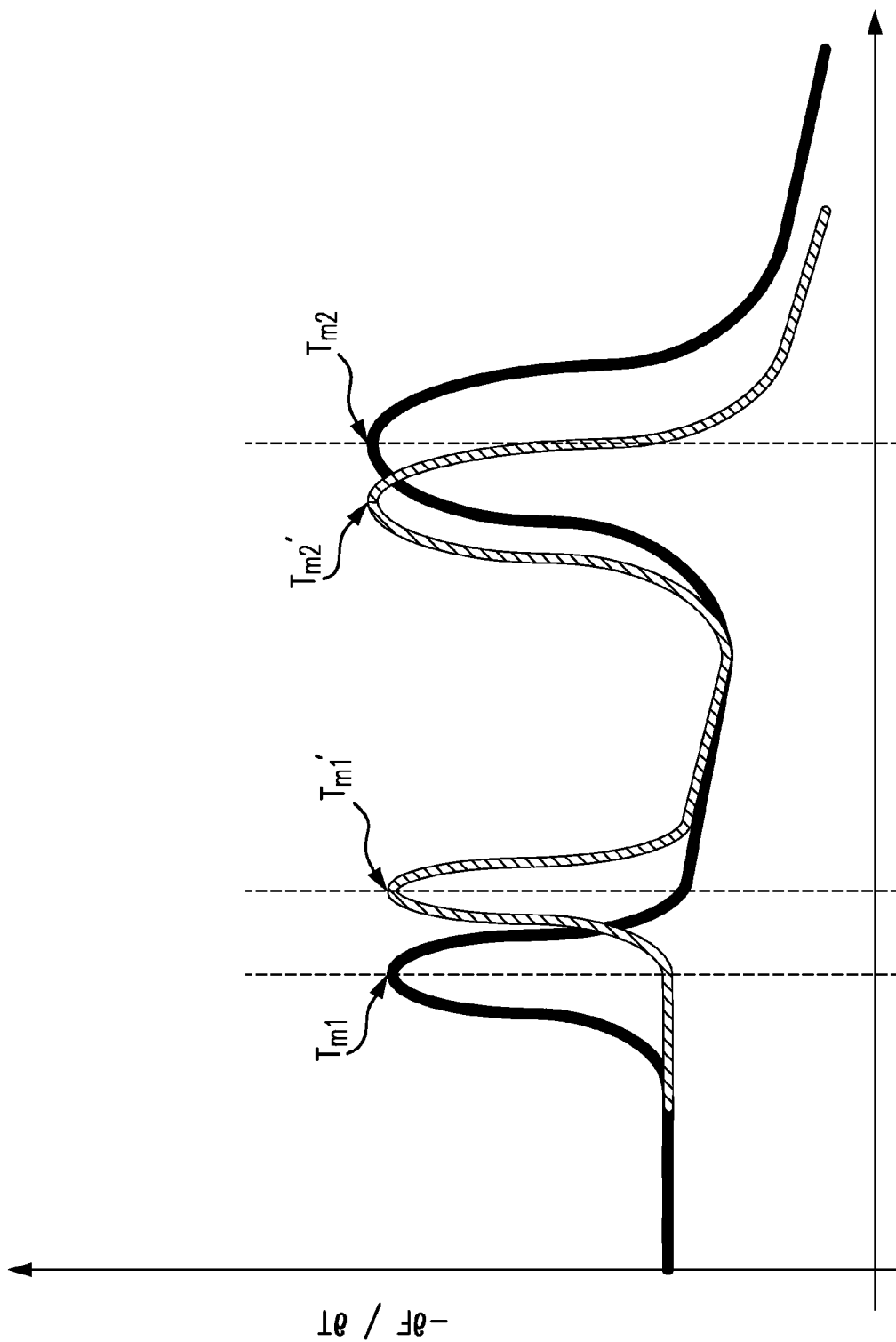
FIG. 6 is an illustration of a first derivative plot of a melt curve generated with initial calibration coefficients and a second plot showing a known melt curve used as a reference for calibration.

Referring back to process 300, at step 304, the apparent temperatures of each feature (e.g., the apparent melt temperatures $T_{m1}'$ and $T_{m2}'$ respectively corresponding to each amplicon) are identified from the in situ thermal response profile generated in step 302. In some embodiments, the apparent temperatures can be determined from the derivative plot using peak-picking. In other embodiments, the apparent temperatures can be determined by cross-correlating the derivative plot with a known template (i.e., an expected thermal response profile) for each feature, or shifting and stretching the thermal response profile to match a predefined template. FIG. 6 illustrates one example of a derivative plot as obtained by step 302 in comparison with a derivative plot template for the same compound calibrator. The template for correlation may come from a third party, from a theoretical prediction (e.g., a nearest-neighbor thermodynamic calculation), or from a training set on a similar instrument, the same instrument, or a "gold standard" instrument. In some embodiments, using a template created with a similar instrument ensures artifacts such as photobleaching, temperature excursions, etc. are consistent between the compound calibrator and the template.

At step 306, the initial calibration coefficients $k_0'$ and $k_1'$ are used to convert the apparent temperatures of each feature (e.g., the apparent melt temperatures $T_{m1}'$ and $T_{m2}'$) into measurement values corresponding to each feature $M_{m1}$ and $M_{m2}$ (e.g., when the measured value is resistance, the measured values $M_{m1}$ and $M_{m2}$ may be resistances $R_{m1}$ and $R_{m2}$ of the thermal control element respectively at the melt transitions of the compound calibrator).

At step 308, the measurement values corresponding to each feature are matched, respectively, with the known true temperatures of each feature (e.g., the true melt temperatures $T_{m1}$ and $T_{m2}$ respectively corresponding to the known melt transitions in the compound calibrator) to determine the calibration coefficients (e.g., $k_0$ and $k_1$ of Equation 1). As long as the number of features in the thermal response profile is greater than or equal to the number of calibration coefficients, the relations between measured values and known true temperatures (e.g., $(M_{m1}, T_{m1})$ and $(M_{m2}, T_{m2})$) can be used to solve a system of equations to determine the calibration coefficients.

The compound calibrators useful in the present invention may be any compound or mixture of compounds that undergo a physical change when subject to a change in temperature. In one embodiment, the compound calibrator may be a nucleic acid that undergoes denaturation (i.e., a "melt"), when subject to a thermal variation. The compound calibrator may be a single nucleic acid having two melting features (e.g., a nucleic acid containing the MTHFR 667 gene, as shown in FIGS. 19-22 of U.S. patent application Ser. No. 12/759,415, which is herein incorporated by reference in its entirety.) Other compounds, such as proteins, protein complexes, or other compounds and complexes that undergo a thermal transition when heated may also be used as compound calibrators. As described above, in some embodiments, the compound calibrator may contain a mixture of two or more amplicons of a nucleic acid. The amplicons in this embodiment may be from any organism's genome including the human genome. In a further embodiment, the amplicons in the compound calibrator could also be from so called "Ultra Conserved" regions of the human genome (so called Ultra Conserved Elements, see, e.g., U.S. Patent Application Ser. No. 61/378, 927, filed Aug. 31, 2010, and U.S. patent application Ser. No. 13/223,258, the entire disclosures of which are incorporated herein).

Further, in another embodiment, one or more amplicons may be entirely synthetic and not found in any organism's genome. In some embodiments, synthetic amplicons may be preferable because the melt characteristics can be finely engineered by varying the number of GC and AT bonds in the amplicon (or amplicons) to alter the melt temperature thereof. Further, the number of base pairs can be designed to alter melt temperature and melt characteristics. Further deletions and other alterations can be used to alter the melt characteristics.

Figure 7:
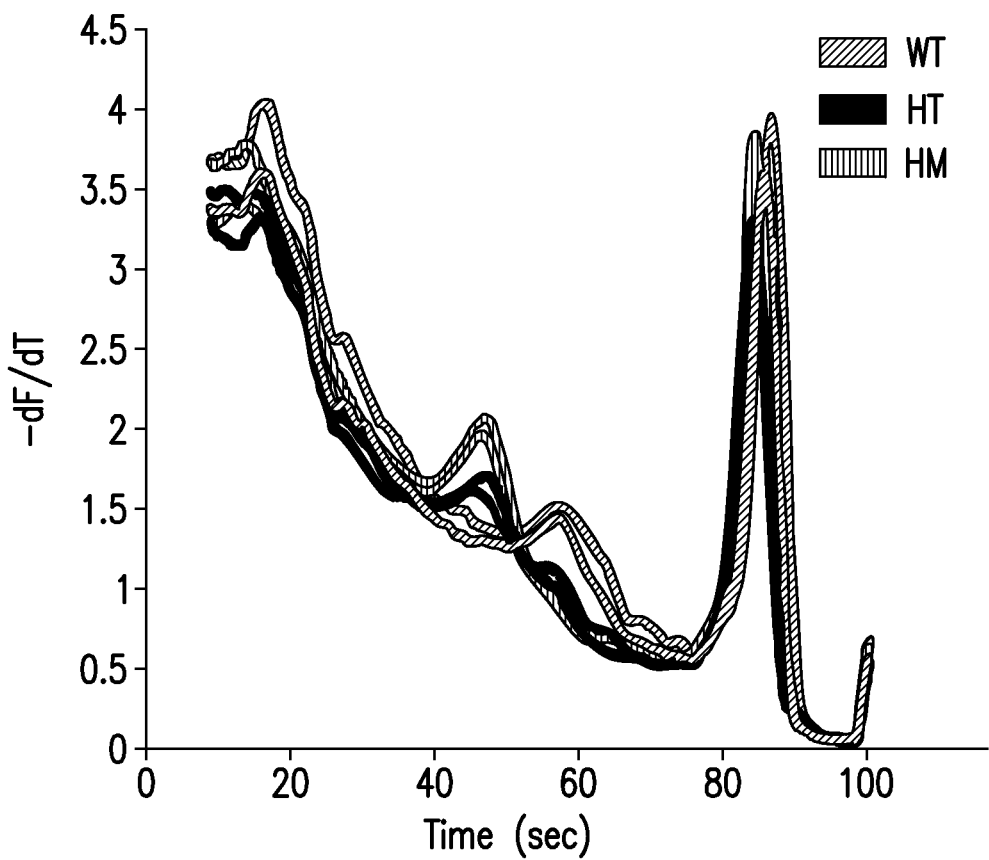
FIG. 7 is an illustration of a first derivative plot of a melt curve for the wild-type, heterozygous, and homozygous mutant genotypes of an amplicon with two melting features that could be used as a compound calibrator in an embodiment of the present invention.

In some embodiments, the compound calibrator may be based on a snap-back or other assay with a probe region separate from the amplicon region. An exemplary embodiment of such compound calibrators is illustrated in FIG. 7 which shows a plot of –dF/dT versus time of a wild type (WT), heterozygous (HT), and homozygous mutant (HM) genotypes. FIG. 7 shows a melt feature associated with the probes between 40 seconds and 60 seconds, which corresponds to a first melt temperature. This could form the first feature in a compound calibrator. There also exists a second feature, which corresponds to the second amplicon at around 85 seconds. The wild type (WT), heterozygous (HT), and homozygous mutant (HM) genotypes shown in this graph all could be suitable compound calibrators because they each have two melt features. Further, while these examples are based on human genomic DNA, different templates (including synthetic DNA templates) may also be appropriate.

In certain embodiments, the compound calibrator will result in a thermal response profile with many easily distinguishable features. Furthermore, the thermal response profile of the compound calibrator will preferably be very repeatable. The compound calibrator preferably exhibits a strong feature signal in comparison to the background and noise level inherent in the measuring instrument. In the instance where thermal melt data is used for the thermal response profile, for example, the melt transition of individual components is preferably much larger than the decay in fluorescence due to temperature in the absence of melting, which allows software to detect the melt transition from the background noise. Also, the melt transition of individual components is preferably large compared to the random variation in fluorescence due to detector limits, which allows software to distinguish a true feature from noise.

Figure 8:
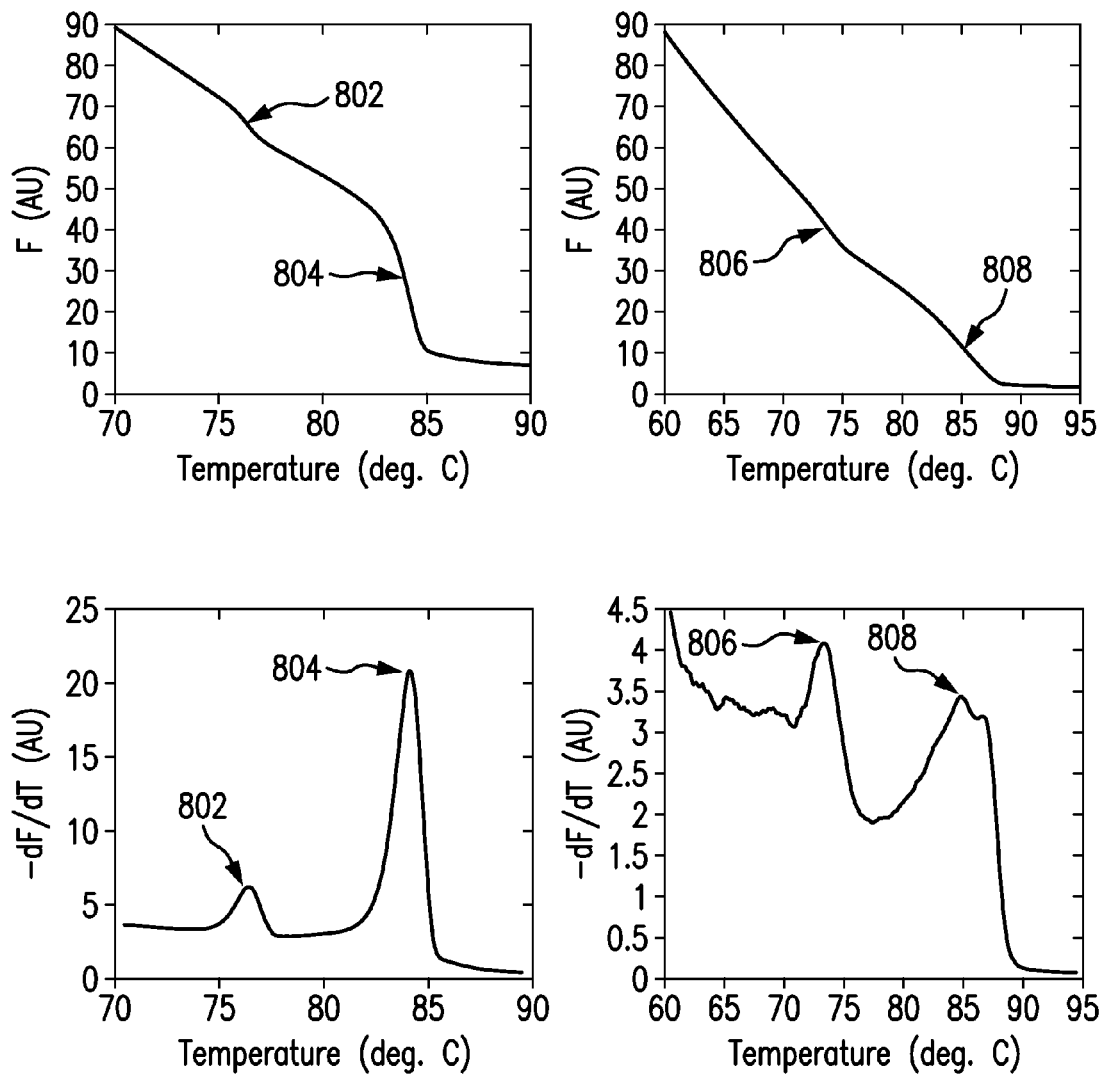
FIG. 8 illustrates a melt curve and a derivative plot for two different compound calibrators that can be used in aspects of the present invention.

FIG. 8 illustrates the desirability of having strong features in the thermal response profile. FIG. 8 is a melt curve and derivative plot for two different compound calibrators. The curves on the left (based on a mixture of amplified DNA from the human genome) show two strong features 802 and 804 which are easily identified from system noise and background. The curves on the right (based on a mixture of oligonucleotides) show feature signals 806 and 808 that are small compared to the background resulting in a derivative plot appears noisy. If one were to use peak picking with the derivative curve on the right, large errors in the apparent $T_m$ would result from the noisy peaks.

The relative relationship between adjacent features can also impact the accuracy of calibration. In some embodiments, if one feature is too small, it may be difficult to distinguish next to the larger feature. Specifically, the smaller feature will appear like it is part of the background. In certain embodiments, the concentrations of the constituents in a compound calibrator containing a mixture of compounds may be adjusted to make the features easier to distinguish. For example, the concentrations of two amplicons may be adjusted to make feature sizes similar. In some embodiments, the molarities of the constituents may be a fixed ratio. In other embodiments, the molarities may be equal, for example, between the first and second compounds in the compound calibrator.

As described above, in some embodiments, the compound calibrator can yield a thermal response profile with three or four or more features. With three features, a quadratic relationship (three calibration coefficients) can be readily determined. With four features, a cubic relationship (four calibration coefficients) can be readily determined. This same concept could be extended to higher orders as well. Further, in some embodiments, the calibration equations need not be polynomial, but could instead follow a number of different mathematical relationships, such as, for example, power law, exponential, logarithmic, and trigonometric relationships. Also as discussed above, with three or four or more features, the additional features could be used to improve the quality of the calibration without using more calibration coefficients (i.e., the system could be over-determined). For example, with 3 features yielding 3 known points, a linear calibration (2 coefficients) can be determined using a least squares fit. Other data fitting techniques could also be used as will be apparent to one skilled in the art, including, for example, both ordinary and total least squares fitting methods. Other examples include those methods that minimize the absolute maximum difference or minimize the sum of absolute differences (e.g., least absolute deviation method) or other robust regression techniques.

Figure 9:
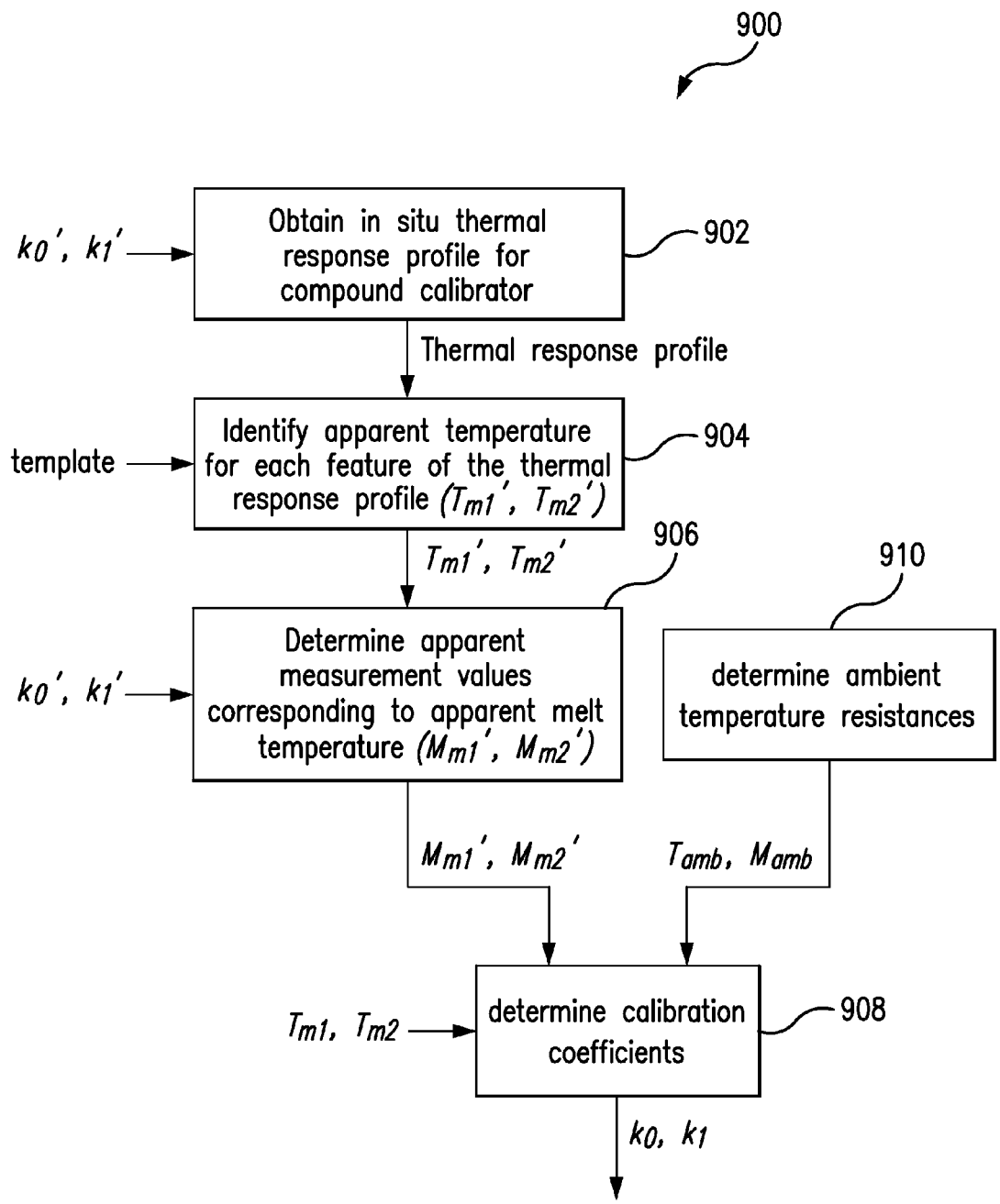
FIG. 9 illustrates a process for calibrating a thermal control element using a compound calibrator according to an embodiment of the present invention.

In some embodiments, the thermal control element can be calibrated using an ambient temperature (i.e., room temperature) in addition to one or more temperatures determined based on features of thermal response profiles. FIG. 9 illustrates a process 900 for calibrating a thermal control element using a compound calibrator according to an embodiment of the present invention. The steps 902, 904, 906 and 908 of the process 900 are substantially equivalent, respectively, to the steps 302, 304, 306, and 308 of the process 300 described above. In addition, the process 900 includes a step 910 of determining the thermal control element's output (e.g., the resistance of the heater 112) while the thermal control element is at a known, ambient temperature. In some embodiments, the ambient temperature can be measured with a separate temperature measurement device such as, for example, a precision RTD or thermocouple. However, any other suitable temperature measurement device including non-contact methods are appropriate as will be understood by those skilled in the art.

In an embodiment, unwanted self-heating of the thermal control element may be minimized. In the embodiment where the thermal control element is a resistive heater, and the measurement value is an electrical characteristic such as resistance, current, applied potential, or other such electrical characteristic, the thermal control element is preferably read using the minimum power or current necessary to obtain an accurate reading. Further, in an embodiment, the ambient temperature calibration point may be defined to include a temperature rise due to self-heating properties of the thermal control element (e.g., $T_{cal}=T_{amb}+\Delta T_{self}$). In some embodiments, self-heating properties of the thermal control element can be determined analytically, with a model, or experimentally.

The measurement value of the thermal control element at the ambient temperature and the ambient temperature define an additional correspondence that, in some embodiments, can be used as a point to define a full-rank system or could be used in an over-determined system to improve the quality of the calibration. For instance, in the embodiment where the measurement value is resistance of the heating element, the measured resistance at ambient temperature (i.e., $R_{amb}$ of the heater 112) and the ambient temperature, (i.e., $T_{amb}$) may define the additional correspondence ($R_{amb}$, $T_{amb}$) that can be used along with two other measured correspondences (e.g., ($R_{Tm1}$,$T_{m1}$) and ($R_{Tm2}$,$T_{m2}$)).

The ambient temperature calibration may be particularly useful in low temperature applications since it may be difficult to create features in a thermal response profile at low temperatures.

Aspects of the present invention can be utilized, for example, in a stopped or continuous flow system or a "stop-and-go" system that alternates between movement and pauses of samples through a microfluidic device.

Aspects of the present invention can be used to calibrate resistive sensors, thermistors, diode temperature sensors, thermocouples, or any other suitable temperature measuring devices. The present invention can further be used to calibrate resistive sensors that are also used for heating such as thin-film platinum elements (or nickel or copper or any other material as would be understood by those skilled in the art).

Embodiments of the present invention can be used in a variety of instruments, but are particularly useful in PCR and thermal melt systems that perform in vitro diagnostics. Embodiments of the present invention can be used to calibrate sensors and heaters that are intended for thermal melt of samples (diagnostics) as well as other heaters and sensors within the instrument that perform entirely different functions (e.g., sample prep or PCR). Other applications are appropriate, such as, for example, machines or systems used for nucleic acid manufacturing or sample preparation, or any application where temperature calibration of a device is desired and/or appropriate.

In one preferred embodiment, the instrument may create sample plugs wherein the plugs contain samples for assays preceded or proceeded by compound calibration plugs. A compound calibration plug may, in one embodiment, be a plug that includes a compound calibrator. The calibration plugs can be loaded and used as needed on whatever frequency the system designers require to maintain the desired accuracy. In another embodiment, the compound calibrator can be introduced to an instrument in a continuous fluid flow prior to the introduction of a sample. In one embodiment, the compound calibrator can be introduced to an instrument and held in place for the duration of the entire calibration.

Figure 10:
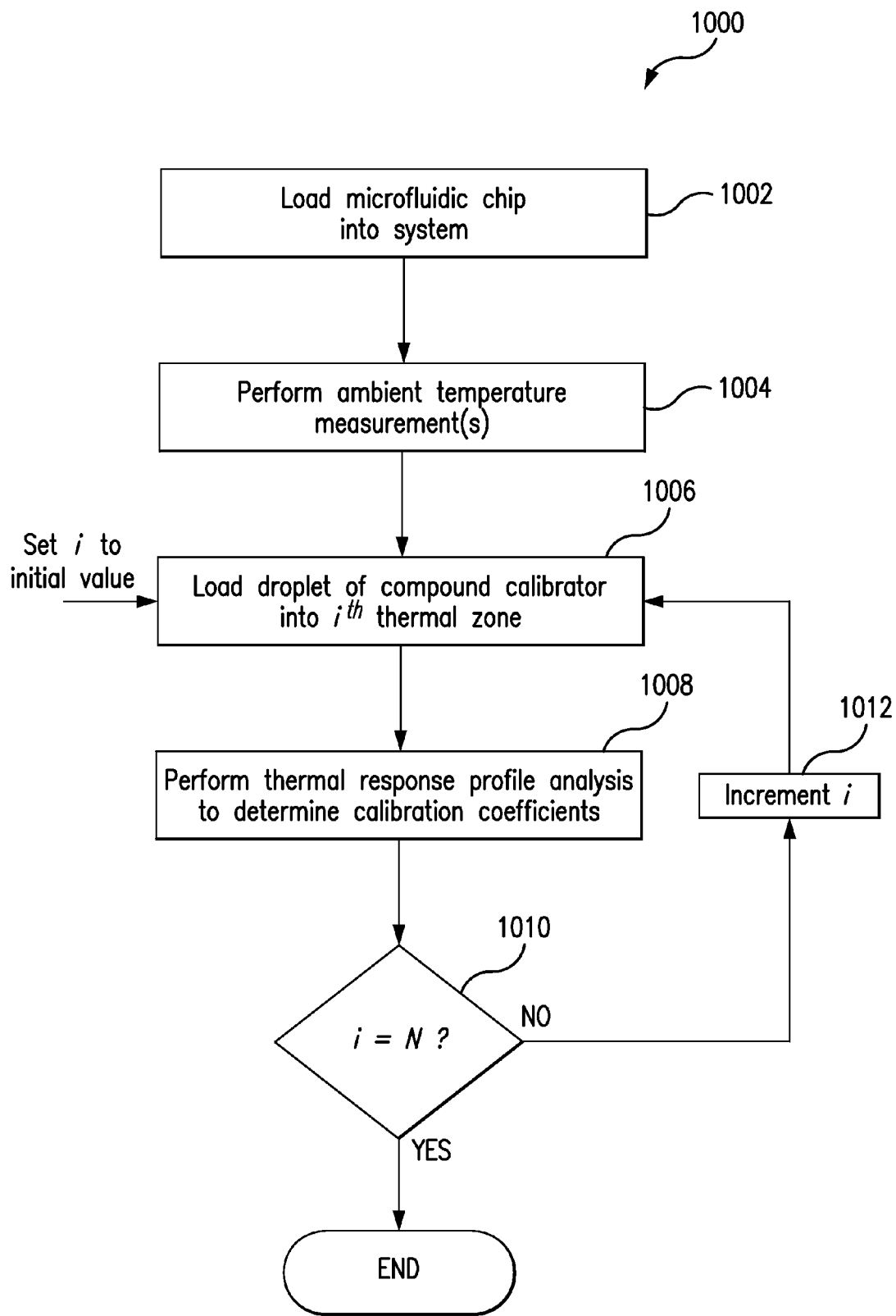
FIG. 10 illustrates a process for calibrating a thermal control element using a compound calibrator according to an embodiment of the present invention.

FIG. 10 illustrates a process 1000 for calibrating a thermal control element using a compound calibrator, in accordance with an embodiment of the present invention. As described below and with reference to FIGS. 10 and 11, the process 1000 can be used to calibrate a multi-zone microfluidic device (one non-limiting example of which is microfluidic chip 100 having a PCR zone 104 and a thermal melt zone 106) in series. In some embodiments, the process 1000 can be performed using a droplet, slug, plug, segment, or continuous flow of compound calibrator that is moving through the microfluidic chip, optionally in series with one or more samples. Although FIG. 10 refers to a droplet of compound calibrator, in practice, the "droplet" can be a slug, plug, segment or continuous flow, for example. At step 1002, the thermal device (e.g., a microfluidic chip) is loaded into a system (e.g., system 200) for controlling and monitoring the reactions in the thermal device. At step 1004, an ambient temperature measurement is performed. In some embodiments, the step 1004 may include the ambient temperature measurement as described above with reference to step 910 of the process 900. In some embodiments, the ambient temperature measurement can be used to adjust one or more of the initial coefficients (e.g., $k_0'$).

Before the next step (step 1006), and index variable (i) is set to an initial value. As described below and illustrated in FIG. 10, the index variable may correspond to the thermal control element being calibrated by the compound calibrator (e.g., when i is equal to n, the $n^{th}$ thermal control element may be calibrated).

Figure 11:
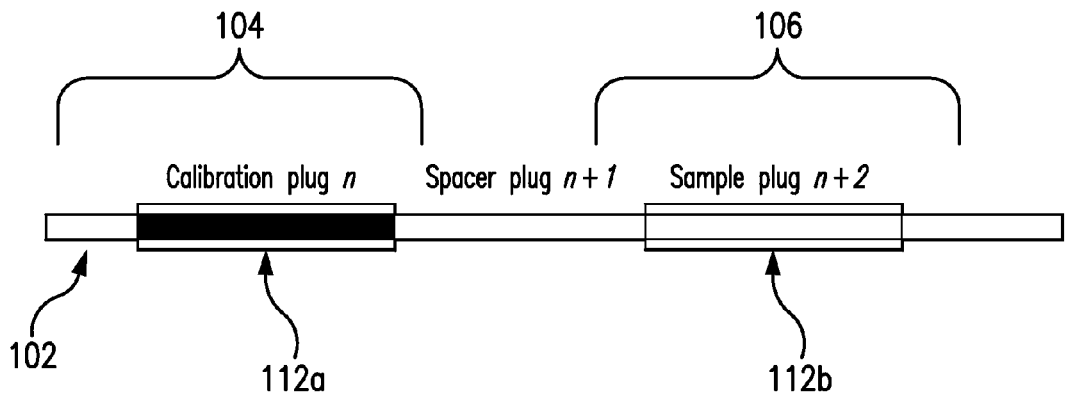
FIG. 11 illustrates a schematic diagram of a microfluidic channel with two thermal zones with a calibration sample occupying the first thermal zone in accordance with aspects of the present invention.

At step 1006, a droplet, plug, slug, segment, or continuous flow of the compound calibrator (e.g., a mixture of two or more amplicons) may be loaded into a first thermal zone. This first thermal zone may be a first thermal zone of a microfluidic chip (e.g., the system 200 may load the compound calibrator into an inlet port 103 and move the compound calibrator to the PCR zone 104 of the microchannel 102). However, the first thermal zone may also be a thermal zone in other applications, such as, for example, a device for sample preparation, DNA extraction, or to "hot start" a polymerase (e.g., Taq). As illustrated in FIG. 11, an assay sample may be present in the next adjacent thermal zone.

At step 1008, a thermal melt analysis is performed to determine the calibration coefficients (e.g., $k_0$ and $k_1$) for the thermal control element associated with the thermal zone (e.g., the heater 112a). In some embodiments, the step 1008 may include one or more of the steps described above with reference to the process 300. As long as the adjacent thermal zones are thermally isolated, an assay sample present in the next adjacent thermal zone may undergo independent processing or analysis in parallel with the calibration of the thermal control element in the first thermal zone.

Figure 12:
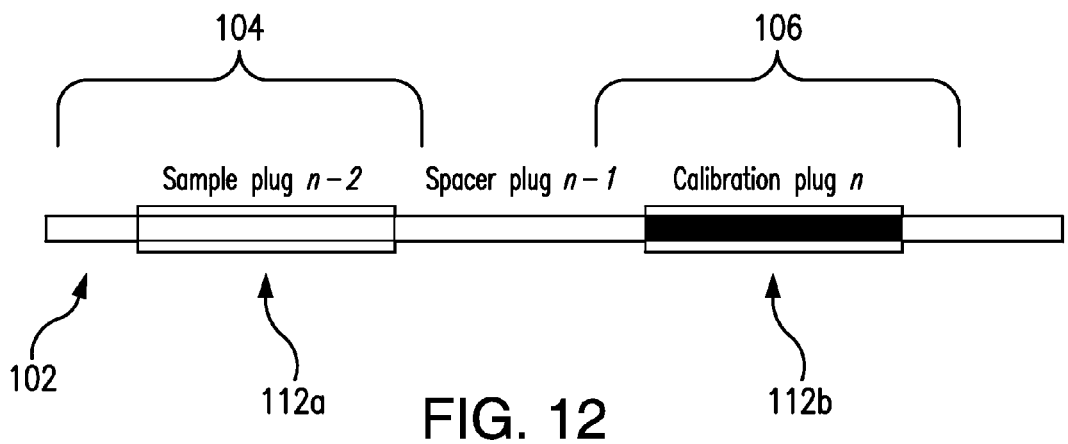
FIG. 12 illustrates a schematic diagram of a microfluidic channel with two thermal zones with a calibration sample occupying the second thermal zone in accordance with aspects of the present invention.

After step 1008, a determination may be made as to whether there are additional thermal control elements to calibrate by checking the index counter against the known number of thermal control elements N in step 1010. If there are additional elements to calibrate, the index counter may be incremented in step 1012 (e.g., i=i+1) and the process 1000 returns to step 1006. The droplet, plug, slug, segment or continuous flow of the compound calibrator may be moved to a next thermal zone of the device (e.g., the system 200 moves the compound calibrator to the thermal melt zone 106). As illustrated in FIG. 12, in some embodiments, this may also include flushing the compound calibrator from the first thermal zone and replacing it with a sample assay (e.g., the system 200 may load a sample into the inlet port 103 and move the sample to the PCR zone 104).

The process 1000 then repeats the step 1008 using the thermal control element associated with the second thermal zone (e.g., using heater 112b). In an alternate embodiment, an assay sample in the first thermal zone may undergo independent processing or analysis in parallel with the calibration of the thermal control element in a second thermal zone. In some embodiments, the second thermal zone may be thermally isolated from the first zone.

In some embodiments, the microfluidic chip may have more than two thermal zones. As illustrated in FIG. 10, the process 1000 repeats the steps of 1006 (i.e., moving the droplet, plug, slug, segment or continuous flow of the compound calibrator to the next thermal zone) and 1008 (i.e., thermal melt analysis) until each thermal zone is calibrated (e.g., until the index variable i is equal to N, where N is the number of thermal control elements to be calibrated).

Figure 13:
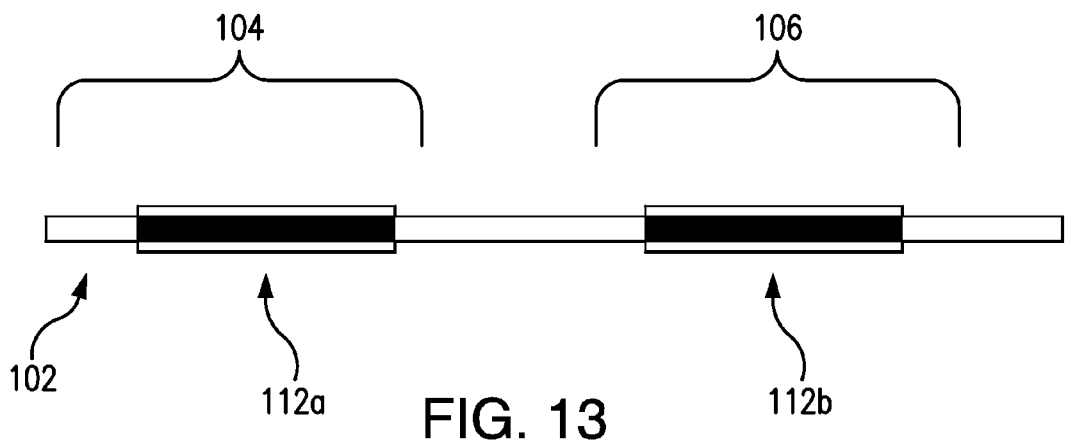
FIG. 13 illustrates a schematic diagram of a microfluidic channel with two thermal zones with a calibration sample occupying both thermal zones in accordance with aspects of the present invention.

In some embodiments where the thermal control elements are thermally isolated, the calibration of thermal control elements along a microfluidic channel (e.g., heaters 112a and 112b along a single microfluidic channel 102) can be performed in parallel. In some embodiments, this can include filling the entire channel with the compound calibrator. As illustrated in FIG. 13, in other embodiments, a separate droplet, plug, slug, segment or continuous flow of the compound calibrator is moved to each thermal control element (e.g., the system 200 moves one droplet to the thermal melt zone 106 and another droplet to the PCR zone 104) and the calibration processes for each thermal control element is performed simultaneously.

Illustrative Example

Using a compound calibrator consisting of amplicons from the sickle cell gene and ultra-conserved element 415 on chromosome 17, a set of calibration data was generated in accordance with the above-described systems and processes.

Figure 14:
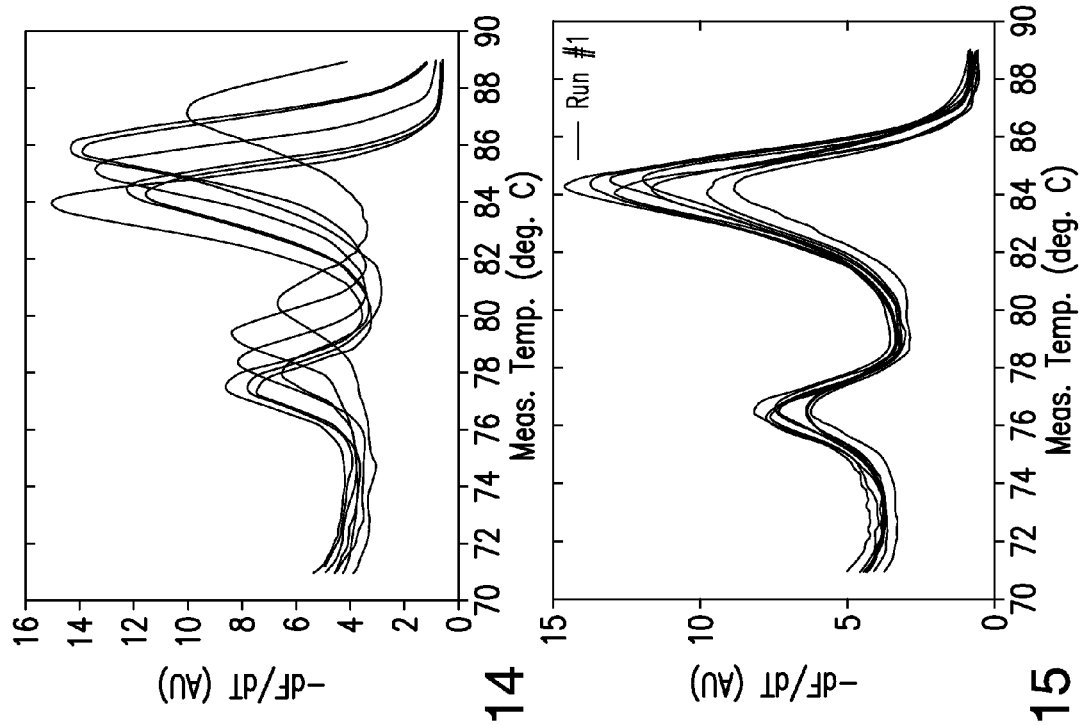
FIG. 14 illustrates thermal melt curves and derivative plots obtained with a microfluidic device prior to a calibration in accord with an embodiment of the present invention.

FIG. 14 illustrates the raw thermal melt curves for uncalibrated thermal control elements and the derivative plots based on those curves, using initial estimated coefficients $k_0'$ and $k_1'$. As can be seen in FIG. 14, the features of the melt curves prior to calibration do not align because of intrinsic variances between different thermal control elements or other inaccuracies in the in situ temperature measurements.

Figure 15:
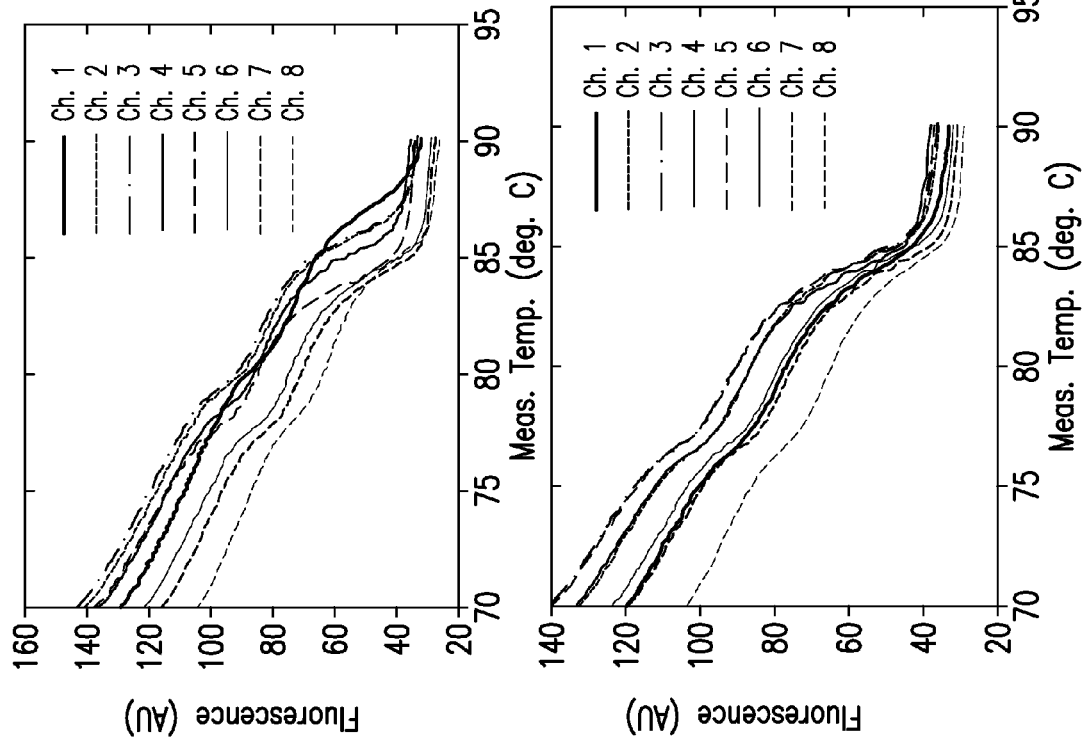
FIG. 15 illustrates thermal melt curves and derivative plots obtained with a microfluidic device subsequent to a calibration in accord with an embodiment of the present invention.

FIG. 15 illustrates the thermal melt curves and derivative plots for the same system after the above described systems and methods were used to determine more accurate values for $k_0$ and $k_1$. As shown in FIG. 15, the present invention resulted in significantly more accurately calibrated thermal control elements (i.e., the features of the melt curves are well aligned with the true known temperatures $T_m$).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A method for calibrating a thermal control element, comprising:
   providing a compound calibrator in thermal contact with said thermal control element, wherein the compound calibrator is a mixture of two or more amplicons of a nucleic acid;
   utilizing said thermal control element to perform a thermal variation on said compound calibrator to generate a thermal response profile for said compound calibrator;
   identifying a first feature of said thermal response profile and generating a first relation between a known temperature of said first feature and a first measurement value of said thermal control element;
   identifying a second feature of said thermal response profile and generating a second relation between a known temperature of said second feature and a second measurement value of said thermal control element;
   calculating one or more calibration coefficients for said thermal control element based on said first and second relations.

2. The method of claim 1, wherein the thermal response profile is a thermal melt curve.

3. The method of claim 2, wherein the first feature is a first melting temperature $T_{m1}$ of the compound calibrator, and wherein the second feature is a second melting temperature $T_{m2}$ of the compound calibrator.

4. The method of claim 1, wherein the measurement value is the resistance of the thermal control element.

5. The method of claim 1, wherein said first feature is at a melting temperature of a first of said two or more amplicons in said compound calibrator, and wherein said second feature is at a melting temperature of a second of said two or more amplicons in said compound calibrator.

6. The method of claim 1, wherein the amplicons are from Ultra Conserved Elements of the human genome.

7. The method of claim 1, wherein the amplicons are synthetically generated.

8. The method of claim 1, wherein the calibration coefficients are the coefficients of a linear calibration equation.

9. The method of claim 1, further comprising the step of identifying a third feature of said thermal response profile and generating a third relation between a known temperature of said third feature and a third measurement value of said thermal control element; and wherein said calculating step comprises calculating one or more calibration coefficients for said thermal control element based on said first, second, and third relations.

10. The method of claim 9, wherein the calibration coefficients are the coefficients of a quadratic calibration equation.

11. The method of claim 9, wherein the number of features identified is greater than the number of calibration coefficients calculated.

12. The method of claim 9, wherein said first feature is at a melting temperature of a first of three or more amplicons of a nucleic acid in said compound calibrator, said second feature is at a melting temperature of a second of said three or more amplicons of a nucleic acid in said compound calibrator, and said third feature is at a melting temperature of a third of said three or more amplicons of a nucleic acid in said compound calibrator.

13. The method of claim 9, wherein one of said first, second, and third features is at a melting temperature of a first amplicon of a nucleic acid in said compound calibrator, and the other two of said first, second, and third features are at melting temperatures of a second amplicon of a nucleic acid in said compound calibrator.

14. The method of claim 1, further comprising the steps of identifying a third relation between a known ambient temperature and measurement value of said thermal control element;
   wherein said step of calculating one or more calibration coefficients is further based at least on said first, second, and third relations.

15. A method for calibrating a thermal control element, comprising:
   providing a compound calibrator in thermal contact with said thermal control element, wherein the compound calibrator is a mixture of two or more amplicons of a nucleic acid;
   utilizing said thermal control element to perform a thermal ramp, generating a melt curve for said compound calibrator;
   identifying a first feature of said melt curve and generating a first relation between a known temperature of said first feature and a first value of said thermal control element;
   identifying a second feature of said melt curve and generating a second relation between a known temperature of said second feature and a second value of said thermal control element;
   calculating one or more calibration coefficients for said thermal control element based on at least said first and second relations.

16. The method of claim 15, further comprising:
   identifying a third relation between a known ambient temperature and a third measurement value of said thermal control element;
   wherein said step of calculating one or more calibration coefficients is further based at least on said third relation.

17. A method for calibrating a thermal control element, comprising:

providing a compound calibrator in thermal contact with said thermal control element, the compound calibrator characterized by first and second known features associated with a first known temperature and a second known temperature, respectively, wherein the compound calibrator is a mixture of two or more amplicons of a nucleic acid;

utilizing said thermal control element to perform a thermal variation on said compound calibrator to measure a thermal response profile for said compound calibrator as a function of temperature;

identifying the first feature of said thermal response profile and generating a first relation between the known temperature of said first feature and a first resistance of said thermal control element, wherein the first resistance is calculated based upon a temperature obtained from the thermal response profile as associated with the first feature;

identifying a second feature of said thermal response profile and generating a second relation between the known temperature of said second feature and a second resistance of said thermal control element, wherein the second resistance is calculated based upon a temperature obtained from the thermal response profile as associated with the second feature;

calculating one or more calibration coefficients for said thermal control element based on said first and second relations defining relationship between a temperature of a thermal control element and a measured resistance of said thermal control element.

18. The method for calibrating a thermal control element of claim 17, further comprising pre-selecting one or more initial calibration coefficients for a calibration equation defining relationship between a temperature of a thermal control element and a resistance of said thermal control element and using the one or more initial calibration coefficients for calculating the first and second resistance of said thermal control element.

* * * * *